(12) United States Patent
Gong et al.

(10) Patent No.: US 7,435,594 B2
(45) Date of Patent: Oct. 14, 2008

(54) SCAFFOLD FOR CULTURING CELLS

(75) Inventors: Jian Ping Gong, Sapporo (JP);
Yoshihito Osada, Sapporo (JP);
Yongmei Chen, Sapporo (JP)

(73) Assignee: Hokkaido University, Hokkaido (JP)

( * ) Notice: Subject to any disclaimer, the term of this patent is extended or adjusted under 35 U.S.C. 154(b) by 360 days.

(21) Appl. No.: 11/050,426

(22) Filed: Feb. 4, 2005

(65) Prior Publication Data

US 2006/0003442 A1    Jan. 5, 2006

(30) Foreign Application Priority Data

Jun. 30, 2004  (JP)  ............................ 2004-194412
Jan. 7, 2005   (JP)  ............................ 2005-002976

(51) Int. Cl.
*C12N 5/00* (2006.01)
*C12N 11/08* (2006.01)

(52) U.S. Cl. ..................... 435/397; 435/180; 435/395

(58) Field of Classification Search .................. None
See application file for complete search history.

(56) References Cited

U.S. PATENT DOCUMENTS 5,369,012 A  * 11/1994 Koontz et al. ............. 435/7.92
6,617,152 B2 *  9/2003 Bryhan et al. ............. 435/283.1
6,855,746 B2 *  2/2005 Yoshitake et al. ............. 522/84
7,022,523 B2 *  4/2006 Tsuzuki et al. ............. 435/401
7,078,458 B2 *  7/2006 Irie et al. ..................... 524/556

OTHER PUBLICATIONS

Chen, Y., et al., "Endothelial Cell Culture on Structure Controlled Polacrylic Acid Hydrogel.: Tailored for Application in Artificial Blood Vessel", $52^{nd}$ *Symposium of the Society of Polymer Science*, Japan, 2 pages, (Sep. 2003).
Shiraishi, N., "Cultivation of Endothelial Cells on Synthetic Polymer Gels", *Summaries of Master Thesis Presentation of the Year Heisei 15* (2003), pp. 2-5, (2003). English translation of Japanese document. With Declaration and English translation of Declaration.

* cited by examiner

*Primary Examiner*—David M Naff
(74) *Attorney, Agent, or Firm*—The Nath Law Group; Joshua B. Goldberg; Susanne M. Hopkins

(57) ABSTRACT

A cell culture scaffold containing a gel having a network structure comprised of a synthetic polymer such that cultured cells spread in a shorter time and the number of adsorbed cultured cells per unit area is larger than in the case of using a gel having a network structure comprised of polyacrylic acid, while taking advantage of synthetic polymers with low manufacturing cost, easy quality control and no risk of virus infection in cultured cell. Used as the cell culture scaffold is a gel containing asynthetic polymer obtained by polymerization or copolymerization of a monomer having a sulfonic group such as p-styrenesulfonic acid sodium salt (NaSS) and 2-acrylamide-2-methylpropane sulfonic acid sodium salt (NaAMPS).

8 Claims, 9 Drawing Sheets

SCAFFOLD FOR CULTURING CELLS

BACKGROUND OF THE INVENTION

1. Field of the Invention

The present invention relates to cell culture scaffold containing gels having a network structure comprised of a synthetic polymer, methods of manufacturing the scaffold and cell culture methods.

2. Description of the Related Art

Conventionally, plastic such as polystyrene coated with collagen has widely been used as cell culture scaffold. Collagen is a fibrous protein constituting connective tissue in multicellular organisms, a biopolymer widely present in nature, however, high in cost required to isolate it from a biological cell or tissue and purify, thus derived from the biological cell or tissue, and therefore, results in problems such that the quality varies with the cell or tissue from which collagen is derived, and that there is a risk of virus infection.

The inventors of the present invention proposed to use synthetic polymers enabling low manufacturing cost, control of quality and no risk of virus infection in cultured cell as a substitute for collagen, found out that bovine endothelial cells adsorb to a surface of a gel and spread thereon if the gel has a network structure comprised of, particularly, Poly-Acryl Acid (PAA) among a plurality of synthetic polymers, and have developed techniques to use the gel as a cell culture scaffold. The techniques are described in Chen, Yongmei, et al., "Endothelial Cell Culture on Structure Controlled Polyacrylic Acid Hydrogel: Tailored for Application in Artificial Blood Vessel" Proceeding of the 52nd Symposium of the Society of Polymer Science, Japan, September, 2003. According to the techniques as described in the aforementioned document, it is possible to culture endothelial cells or the like to confluent or sub-confluent on a gel having PAA which surface is not modified with a factor that promotes growth of cells.

However, in the techniques as described in the document, there are problems that a spreading rate of endothelial cell is lower and culture time is longer required for endothelial cell to reach confluent or sub-confluent than in the case of culturing endothelial cells using collagen.

The techniques as described in the document further have a problem that cells such as endothelial cells cannot be cultured to confluent or sub-confluent on the gel having PAA, unless the degree of crosslinking of PAA falls within a limited range of less than 4 mol %.

Furthermore, in the techniques as described in the document, in the case of providing the gel with strength needed as a cell culture scaffold, since the degree of crosslinking of PAA cannot be increased as described above, for example, the network structure comprised of PAA is entangled with a network structure comprised of another polymer, there by complicating processes of manufacturing the gel.

SUMMARY OF THE INVENTION

It is an object of the present invention to provide a cell culture scaffold containing a gel having a network structure comprised of a synthetic polymer such that cultured cells spread in a shorter time and the number of adsorbed cultured cells per unit area is larger than in the case of using a gel having a network structure comprised of polyacrylic acid, while taking advantage of synthetic polymers with low manufacturing cost, easy quality control and no risk of virus infection in cultured cell.

According to an aspect of the invention, a cell culture scaffold of the present invention adopts a structure containing a gel having a network structure comprised of a synthetic polymer obtained by polymerization or copolymerization of a monomer having a sulfonic group. According to another aspect of the invention, in the above invention, the cell culture scaffold of the present invention adopts a structure where the monomer having a sulfonic group is an aromatic compound.

According to still another aspect of the invention, in the above invention, the cell culture scaffold of the present invention adopts a structure where the monomer having a sulfonic group is a p-styrene sulfonic acid alkali metal salt or 2-acrylamide-2-methylpropane sulfonic acid alkali metal salt.

According to a further aspect of the invention, in the above invention, the cell culture scaffold of the present invention adopts a structure where the molar fraction of p-styrenesulfonic acid alkali metal salt as a structural unit is 6 mol % or more in the syntheticpolymer.

According to a still further aspect of the invention, in the above invention, the cell culture scaffold of the present invention adopts a structure where the molar fraction of 2-acrylamide-2-methylpropane sulfonic acid alkali metal salt as a structural unit is 30 mol % or more in the synthetic polymer.

According to a yet further aspect of the invention, in the above invention, the cell culture scaffold of the present invention adopts a structure where the degree of crosslinking ranges from 0.1 mol % to 10 mol % in the synthetic polymer.

According to a yet further aspect of the invention, in the above invention, the cell culture scaffold of the present invention adopts a structure where the network structure comprised of the synthetic polymer is present on the uppermost layer of the surface of the gel.

According to a yet further aspect of the invention, a cell culture scaffold of the present invention adopts a structure containing a gel having an interpenetrating polymer network structure in which a network structure comprised of a synthetic polymer obtained by polymerization or copolymerization of p-styrenesulfonic acid alkali metal salt or 2-acrylamide-2-methylpropane sulfonic acid alkali metal salt penetrates a network structure comprised of a polymer having a crosslinking structure, or a semi-interpenetrating polymer network structure in which the synthetic polymer is a linear polymer and the linear synthetic polymer penetrates the network structure with the crosslinking structure.

According to a yet further aspect of the invention, in the above invention, the cell culture scaffold of the present invention adopts a structure where the network structure comprised of the polymer having the crosslinking structure is bacteria cellulose.

According to a yet further aspect of the invention, in a method of manufacturing a cell culture scaffold according to the present invention, in generating a gel having a network structure comprised of a synthetic polymer obtained by copolymerization of a monomer having a sulfonic group, surface potential of the gel is adjusted by adjusting a molar fraction of another monomer subjected to the copolymerization relative to the monomer having the sulfonic group.

According to a yet further aspect of the invention, in a cell culture method according to the present invention, the cell culture scaffold according to the invention is used.

BRIEF DESCRIPTION OF THE DRAWINGS

The above and other objects and features of the invention will appear more fully hereinafter from a consideration of the following description taken in connection with the accompanying drawing wherein one example is illustrated by way of example, in which.

DETAILED DESCRIPTION OF THE PREFERRED EMBODIMENTS

It is a gist of the present invention to use, as a cell culture scaffold, a gel containing a synthetic polymer obtained by polymerization or copolymerization of a monomer having a sulfonic group such as a p-styrenesulfonic acid alkali metal salt, e.g. p-styrenesulfonic acid sodium salt (NaSS), and 2-acrylamide-2-methylpropane sulfonic acid alkali metal salt, e.g. 2-acrylamide-2-methylpropane sulfonic acid sodium salt (NaAMPS).

Embodiments and examples of the present invention will specifically be described below with reference to accompanying drawings as appropriate.

Figure 1:
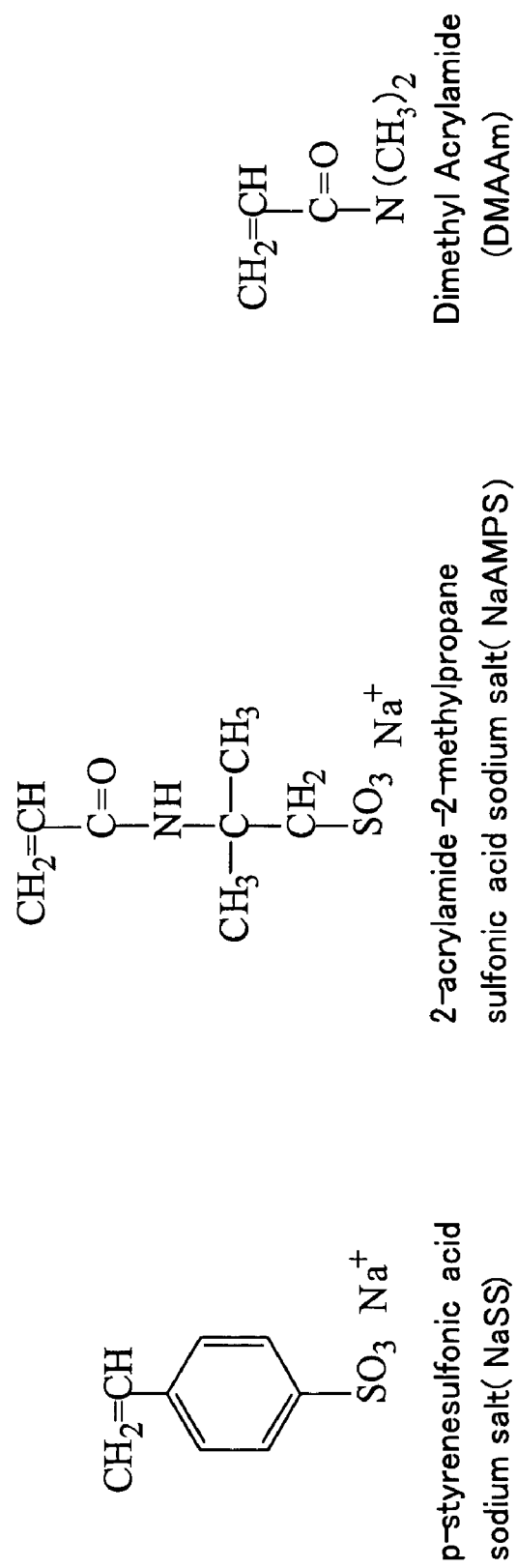
FIG. 1 is a view showing structural formulas of p-styrenesulfonic acid sodium salt and 2-acrylamide-2-methylpropane sulfonic acid sodium salt.

A cell culture scaffold according to the present invention has a structure containing a gel having a network structure comprised of a synthetic polymer obtained by polymerization or copolymerization of a monomer having a sulfonic group such as NaSS and NaAMPS. FIG. 1 shows structural formulas of NaSS, NaAMPS and dimethyl acrylamide (DMAAm) as a reference.

On the surface of the gel having a network structure comprised of the synthetic polymer resulting from polymerization or copolymerization of a monomer having a sulfonic group such as NaSS and NaAMPS, as proved in examples described later, cultured cells spread promptly and reach to confluent or sub-confluent in a shorter time than those on the surface of the gel having a network structure comprised of a synthetic polymer obtained by polymerization or copolymerization of acrylic acid (AA) and/or DMAAm While a specific mechanism to generate such a phenomenon has not been clarified, the inventors of the present invention assume that the charge density on the gel surface is important to cell culture, and by using the monomer having a sulfonic group, the surface potential of the synthetic polymer obtained by polymerization or copolymerization of the monomer falls with a range suitable for cell culture. It is generally known that a cell adheres to scaffold via an adhesive protein to grow. Known as such an adhesive protein are fibronectin, laminin, vitronectin and so on. By experiments of the inventors of the present invention with attention directed to laminin, it was conformed that a larger number of laminin adsorbs to the surface of a gel with a higher cell adhesion rate or cell spreading rate. Based on the experiment result, the inventors of the present invention presume that in the case where the gel surface is negatively charged, adhesive proteins present in a blood serum used in cell culture are absorbed to the gel surface, the absorption promotes cell adhesion, and an environment is formed which is further suitable for cell culture.

In view of the fact that the charge density on the gel surface is important to cell culture, the present invention is specified from a following aspect. In other words, the present invention is specified from the aspect where "in generating a gel having a network structure comprised of a synthetic polymer obtained by copolymerization of a monomer having a sulfonic group, surface potential of the gel is adjusted by adjusting a molar fraction of another monomer subjected to the copolymerization relative to the monomer having the sulfonic group". In addition, the "another monomer subjected to the copolymerization to the monomer having the sulfonic group" is, for example, DMAAm. Similarly, the present invention is specified from another aspect where "a network structure comprised of the synthetic polymer is present on the uppermost layer of the surface of the gel having the network structure comprised of the synthetic polymer obtained by polymerization or copolymerization of a monomer having a sulfonic group".

Further, in the synthetic polymer, the molar fraction of p-styrenesulfonic acid alkali metal salt (monomer) as a structural unit is preferably 6 mol % or more, while the molar fraction of 2-acrylamide-2-methylpropane sulfonic acid alkali metal salt (monomer) as a structural unit is preferably 30 mol % or more. The sulfonic group is a strong electrolyte, and therefore, even if the molar fraction thereof is relatively low, 6 mol % or 30 mol %, has dominant effects on characteristics of the surface of the synthetic polymer, thereby enabling the surface to have the charge density suitable for absorption and spreading of cells. The fact that the lower limit of a preferable range of the molar fraction of p-styrenesulfonic acid alkali metal salt is lower than the lower limit of a preferable range of the molar fraction of 2-acrylamide-2-methylpropane sulfonic acid alkali metal salt was obtained from experimental results of examples as described later. As a main factor for the fact, it is considered that p-styrenesulfonic acid alkali metal salt is an aromatic compound with a sulfonic group coupled thereto. In other words, in aromatic compounds with a sulfonic group coupled thereto such as NaSS, since delocalization of electrons occurs due to the interaction between a benzene ring and sulfonic group, the alkali metal ion tends to ionize, and the anchorage increases to which the adhesive protein adsorbs. Therefore, it is considered that a state of the surface of the synthetic polymer suitable for absorption and spreading is formed with an amount of NaSS smaller than an amount of 2-acrylamide-2-methylpropane sulfonic acid alkali metal salt that does not contain a benzene ring. Accordingly, based on the inference from the experimental results, it is said that the monomer having a sulfonic group in the synthetic polymer is preferably an aromatic compound.

Further, the degree of crosslinking in the synthetic polymer obtained by polymerization or copolymerization of NaSS or NaAMPS preferably ranges from 0.1 mol % to 10 mol %. When the degree of crosslinking is less than 0.1 mol %, a network structure required to maintain a gel state as a solid is hard to form, and if such a network is formed, the gel having the network structure has a low modulus, and therefore, cannot provide resistance necessary for a cell to adhere, deform and move. Meanwhile, when the degree exceeds 10 mol %, the gel having the network structure comprised of the synthetic polymer is very hard, extremely low in resistance to deformation, lacks dynamical strength, and is thereby hard to handle.

Figure 2:
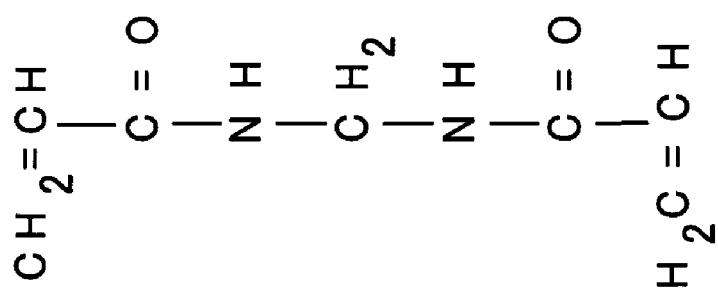
FIG. 2 is a view showing a structural formula of N-N'-methylene-bis(acrylamide)

As a crosslinking agent used in copolymerizing NaSS or NaAMPS to generate a synthetic polymer, types thereof are not limited particularly, and for example, there are N,N'-methylene-bis(acrylamide) (MBAA) and ethylene glycol dimethacrylate. For reference, FIG. 2 shows a structural formula of MBAA. In addition, in the case of using a crosslinking agent such as MBAA, a network structure comprised of a synthetic polymer is formed by radical polymerization. As examples of the other methods of forming the network structure comprised of a synthetic polymer, there are a method of adding a crosslinking agent having a bifunctional or polyfunctional group to a high-density polymer solution to cause intermolecular crosslinking of the polymer, and a method of synthesizing a gel by irradiation with gamma rays.

While the gel is allowed to have any value with respect to the degree of swelling in deionized water, the degree of swelling in buffer solution (for example, N-[2-hydroxyethyl]piperazine-N'-[2-ethanesulfonic acid]:$C_8H_{18}N_2O_4S$ solution) is preferably in a range of 10 to 45. The gel with the degree of swelling of 10 to 45 in buffer solution is provided with appropriate elasticity and flexibility, has strength to such an extent that the gel does not collapse in processing its shape with a utility knife or the like or carrying the gel with tweezers or the like, and therefore, is easy to handle. In addition, it is preferable that this buffer solution has almost the same ionic strength as that of the serum medium used in cell culture. This is because such a buffer solution enables variations in degree of swelling of the gel to be minimized even when the gel is added to the serum medium immediately before cell culture.

Further, it is preferable that the gel has an interpenetrating polymer network structure in which a network structure comprised of a synthetic polymer obtained by polymerization or copolymerization of a monomer having a sulfonic group such as NaSS and NaAMPS penetrates a network structure comprised of a polymer having a crosslinking structure, or a semi-interpenetrating polymer network structure in which the synthetic polymer is a linear polymer and the linear synthetic polymer penetrates the network structure with the crosslinking structure. Such a gel with the interpenetrating polymer network structure or semi-interpenetrating polymer network structure is extremely high in dynamical strength, and thus is easy to handle (for example, see International Publication No.03/093337). Furthermore, when the gel has a interpenetrating polymer network structure or semi-interpenetrating polymer network structure, in addition to improvements in durability such that repeated use is allowed, it becomes possible to perform cell culture in environments such that vibration and/or pressure is applied, and thus, the shape processing is further easier. In addition, the "interpenetrating polymer network structure" indicates a network structure where a network structure as a base is entangled with another network structure, while the "semi-interpenetrating polymer network structure" indicates a network structure where a network structure as a base is entangled with a linear polymer.

In the gel thus having the interpenetrating polymer network structure or semi-interpenetrating polymer network structure, since "a network structure as a base" is entangled with "another network structure or linear polymer", the uppermost layer of the surface is almost covered with the "another network structure or linear polymer". Accordingly, characteristics of the "another network structure or linear polymer" are dominant in characteristics on the uppermost layer of the surface of the gel. Therefore, by using a synthetic polymer obtained by polymerization or copolymerization of a monomer having a sulfonic group as the "another network structure or linear polymer", it is possible to set the uppermost layer of the surface of the gel for a state suitable for adsorption and spreading of cells. Further, in the case where radical polymerization is carried out, for example, by irradiation with ultraviolet rays in polymerizing or copolymerizing the monomer having a sulfonic group to generate the "another network structure or linear polymer", when a range and shape are preset to carry out irradiation with ultraviolet rays, it is possible to culture cells in a desired range and desired shape on the uppermost layer of the surface of the gel.

Meanwhile, in the gel having the interpenetrating polymer network structure, or semi-interpenetrating polymer network structure, the "network structure as a base" does not have a direct effect on adsorption and spreading of cells, therefore, does not need to be the synthetic polymer obtained by polymerization or copolymerization of a monomer having a sulfonic group, and may be, for example, a neutral synthetic polymer comprised of DMAAm. Further, the "network structure as a base" preferably has the function of increasing the strength of the gel, and as a network structure having such a function, there is bacteria cellulose (BC), for example. BC is a hydrogel generated by specific acetic acid bacteria, and has characteristics such that network intervals are wide, fibers constituting the network structure are thick, and physical crosslinking is present such as entanglement and hydrogen bond, as compared with the network structure comprised of a general synthetic polymer such as DMAAm. In BC cultured by stationary culture, since extremely thin fibers form a layer structure therein, the dynamical strength is isotropic, and high extensile strength appears in the direction parallel to the layers. More specifically, when the inventors of the present invention prepared gels by combining BC and gelatin, the gels indicated high physical properties with initial modulus of 4 MPa and rupture stress of 5 MPa at maximum in compressive stress, and with initial modulus of 2.1 MPa and rupture stress of 4 MPa in tensile stress.

In polymerizing or copolymerizing NaSS or NaAMPS, it may be possible substituting another substance except Na for a counter ion of the sulfonic group of NaSS or NaAMPS, and re-substituting Na for the counter ion by ion exchange after generating the synthetic polymer.

Cell culture scaffold according to the present invention are not limited particularly in form, as long as the scaffold contain the gel as described above. For example, the gel may only be placed in a Petri dish. Further, it may be possible to process the gel to fine particles or porous member. By constituting a cell culture scaffold using thus processed gel, it becomes possible to three-dimensionally use the surface of the gel as anchorage of cell culture, and it is thereby possible to drastically improve efficiency in cell culture. Such a three-dimensional cell culture method is preferably used in cells particularly suitable for high-density culture.

It is possible to use the cell culture scaffold according to the present invention as cell culture scaffold for various kinds of cells. Using the cell culture scaffold according to the present invention, the inventors of the present invention actually cultured bovine fetal aorta endothelial cell (BFAEC), human umbilical vein endothelial cell (HUVEC) and fibrolast of rabbit synovia. As a result, it was confirmed that using the cell culture scaffold according to the present invention allows the three kinds of cells to proliferate to confluent with reliability.

In a cell culture method according to the present invention, it is preferable that the gel contains therein a liquid factor suitable for growth of cell to be used in cell culture. Thus culturing cells is capable of further increasing a spreading rate in cell culture. In this case, by choosing an appropriate liquid factor, without being limited to endothelial cells, it is possible to provide culture methods suitable for various cell cultures.

In addition, the gel having a network structure comprised of a synthetic polymer obtained from polymerization or copolymerization of NaSS or NaAMPS essentially does not need particular processing to promote adsorption of cultured cell, but the present invention does not eliminate such particular processing. For example, it may be possible to react the synthetic polymer obtained by polymerization or copolymerization of NaSS or NaAMPS with RGD peptide in which arginine, glycin and asparagine acid are bound in this order to promote adsorption of cultured cell to the gel.

Moreover, described in the present invention is the gel having a network structure comprised of a synthetic polymer obtained by polymerization or copolymerization of a monomer having a sulfonic group, but it is presumed that an environment suitable for cell culture is formed when the surface of the gel is negatively charged as described above, and therefore, the present invention is capable of being applied to cell culture scaffold containing a gel having a network structure comprised of a synthetic polymer obtained by polymerization or copolymerization of a monomer having a "sulphonyl" or "phosphoric" group.

The cell culture scaffold and cell culture methods according to the present invention will be described more specifically below with reference to examples.

EXAMPLE 1

1 mol/L of NaSS (Nw=206.20, Tokyo Kasei Kogyo Co., Ltd.) solution was purified by recrystallization with methanol. Four portions separated from purified NaSS were mixed with crosslinking agents MBAA (Wako Pure Chemical Industries Ltd.) so that the agents were 4, 6, 8 and 10 mol/ % to NaSS, respectively. Each of the mixtures of NaSS and MBAA and initiator potassium peroxodisulfate ($K_2S_2O_8$) (Nw=270.32, Kanto Kagaku) were dissolved in pure water in a predetermined concentration, stirred sufficiently and then subjected to bubbling with nitrogen ($N_2$) for 30 minutes. Subsequently, these solutions were poured into glass plates, inserted into ziploks with water prevented from entering, and polymerized by heat in a water bath for 12 hours, thereby generating gels each having a network structure comprised of a synthetic polymer that is a copolymer of NaSS and MBAA with the degree of crosslinking of 4, 6, 8 or 10 mol %. The generated gels were swollen in a large amount of pure water for about a week to be an equilibrium swollen state.

The gels were immersed in a buffer solution of pH 7.4 (117 mM/NaCl+5 mM/HEPES (N-[2-hydroxyethyl]piperazine-N'-2[-ethanesulfonic acid] ($C_8H_{18}N_2O_4S$, Mw=238.3) )+15 mM/$NaHCO_3$) for solvent exchange. Then, a required amount of each of the gels was placed on a Petri dish, and subjected to autoclave sterilization (121° C., 20 minutes). Each sterilized dish was placed on a clean bench, the solvent was removed by suction, a serum-free culture medium was added, and the dish was left in an incubator of 37° C. for more than a day. Separately, a serum culture medium, PBS (Phosphate Buffered Saline) and trypsin solution were heated in a thermostat bath of 37° C.

Subcultured bovine fetal aorta endothelial cells (BFAEC) were set on each of the gels in the dish. The medium was sucked from a T75 flask with a Pasteur pipette and added to each dish, 6 ml of PBS was further added to each dish with a 10 ml Komagome pipette, the endothelial cells were washed, and PBS was removed from the dish by suction. Subsequently, 3 ml of trypsin solution was added to each dish with a 10 ml Komagome pipette, the dish was allowed to stand for several dozen seconds. Subsequently, 7 ml of serum culture scaffold was added to each dish, and pipetting was sufficiently carried out.

The concentration ($X \times 10^4$ cells/ml) of the endothelial cells at this point was measured using an erythrocytometer. Six hours after the endothelial cells were set on the gel in the dish, a state of culture of the endothelial cells in each dish was observed with a phase-contrast microscope (OLYMPUS Cooperation, IX71), while being shot with a digital camera (OLYMPUS Cooperation, DP12-B). Based on the shot pictures, a cultured endothelial cell extending pseudopod in the shape of a spindle or star is counted as a spreading cell, while a cell in the shape of a circle is counted as an adsorption cell, whereby "the number of spreading cells" and "the number of adsorption cells" were measured on all the shot pictures. Further, using the phase-contrast microscope and digital camera, observations of the state of culture of endothelial cells were continued every 24 hours.

Figure 3:
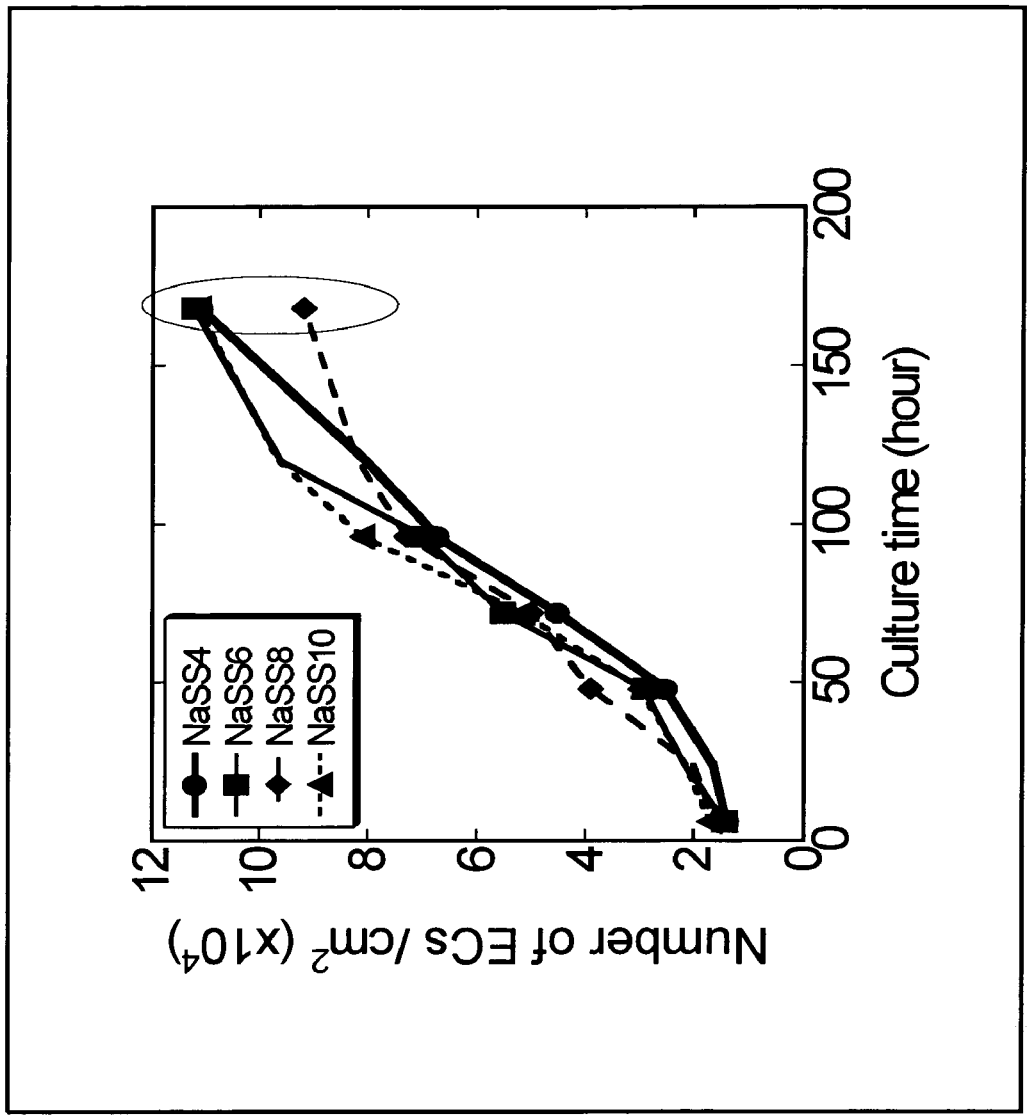
FIG. 3 is a graph showing, for each degree of crosslinking, variations in the number of spreading endothelial cells with culture time in a gel generated by copolymerization of p-styrenesulfonic acid sodium salt.
Figure 5:
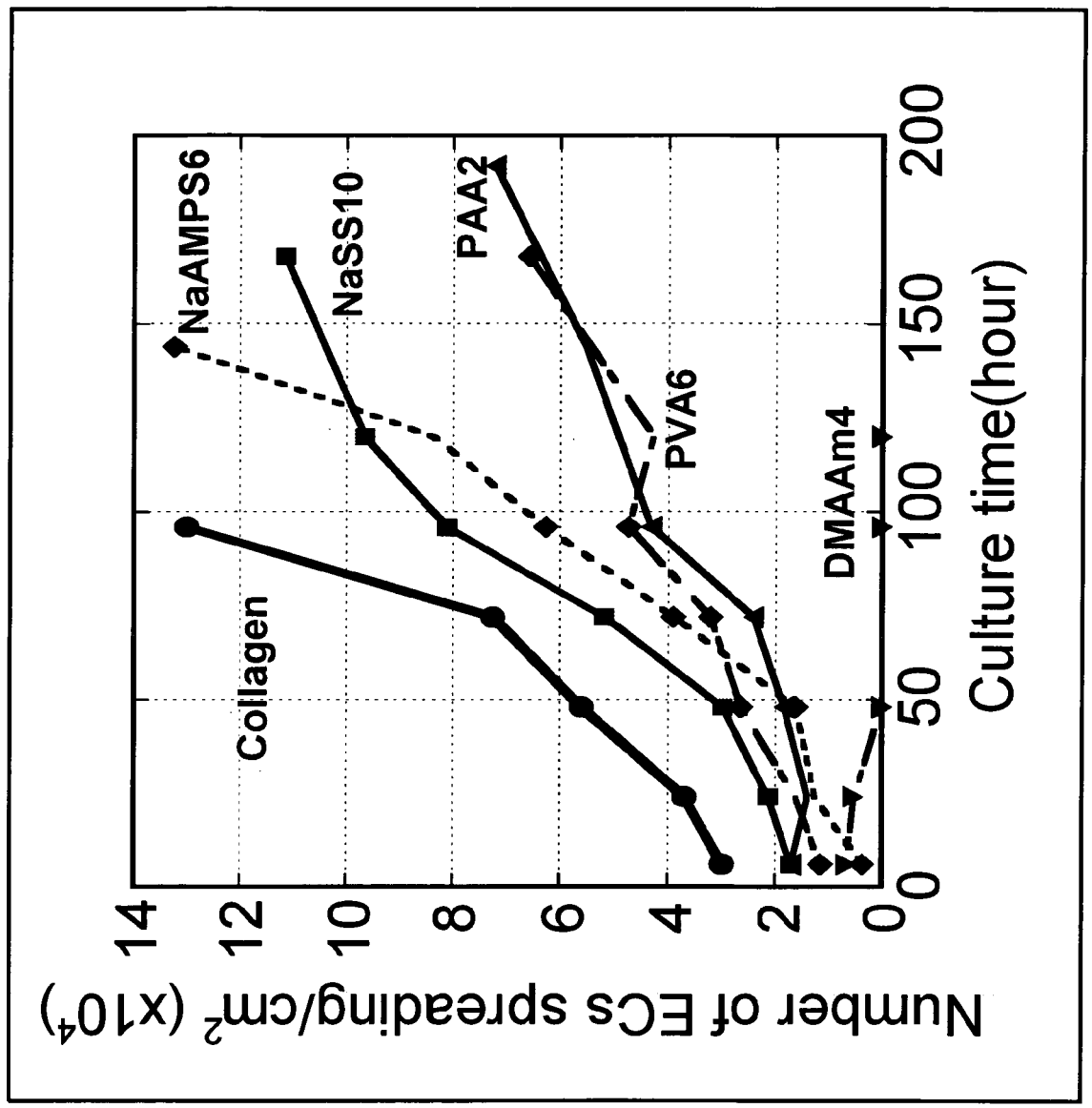
FIG. 5 is a graph showing variations in the number of spreading endothelial cells with culture time on a gel of each of examples and comparative examples.

FIG. 3 shows variations in the number of spreading cells with measurement time among the endothelial cells on gels with different degrees of crosslinking. In the example in FIG. 3, NaSS4 represents the gel with the degree of crosslinking of 4 mol %, NaSS6 represents the gel with the degree of crosslinking of 6 mol %, NaSS8 represents the gel with the degree of crosslinking of 8 mol %, and NaSS10 represents the gel with the degree of crosslinking of 10 mol %. FIG. 5 shows variations in the number of spreading cells with time with respect to NaSS10 (■ in FIG. 5).

EXAMPLE 2

Figure 4:
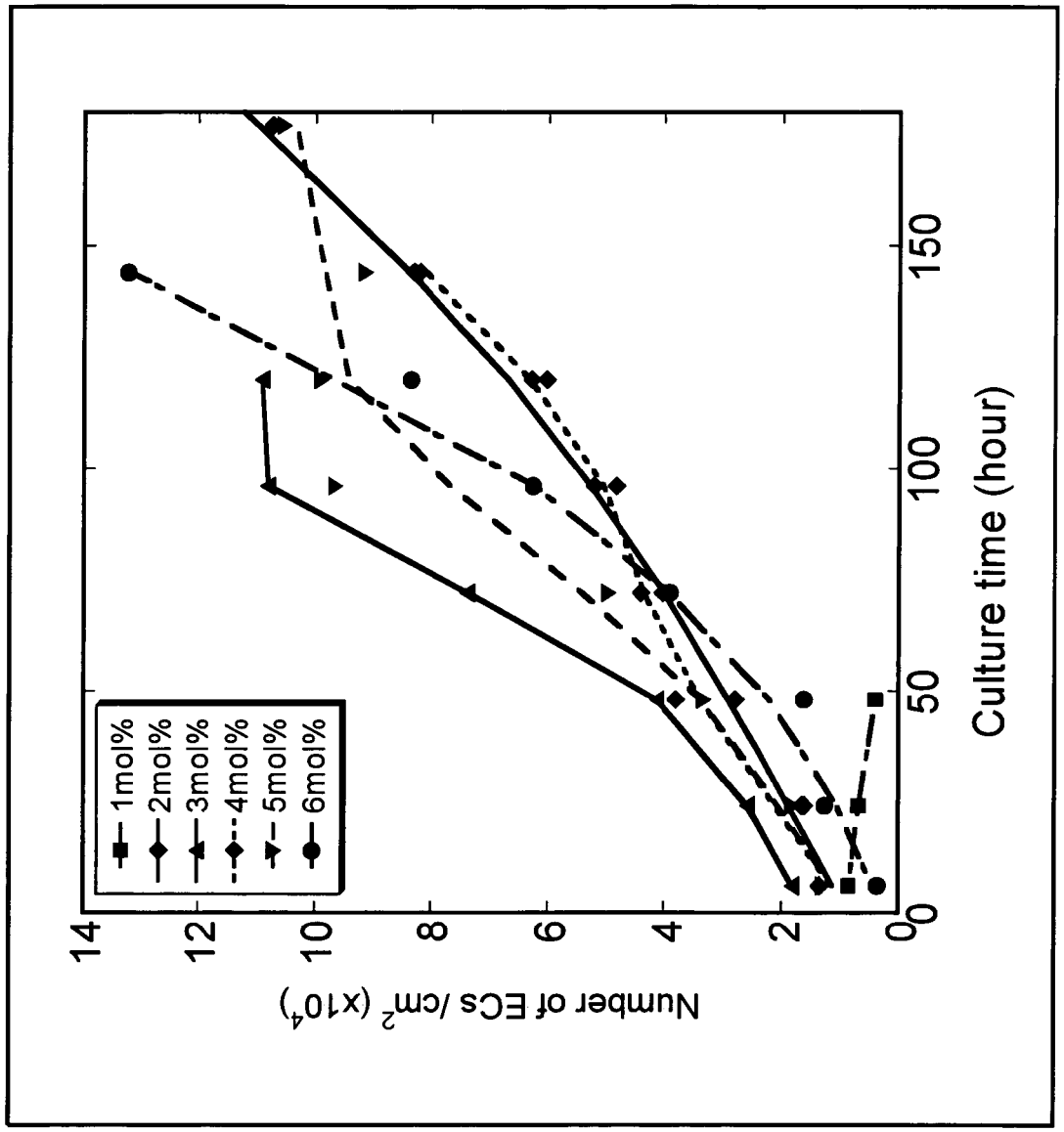
FIG. 4 is a graph showing, for each degree of crosslinking, variations in the number of spreading endothelial cells with culture time in a gel generated by copolymerization of 2-acrylamide-2-methylpropane sulfonic acid sodium salt.

Gels were prepared and the number of spreading cells among endothelial cells was measured in the same way as in example 1, except that NaAMPS (Tokyo Kasei Kogyo Co., Ltd.) was substituted for NaSS, and that crosslinking agents MBAA were mixed into NaAMPS respectively in 1, 2, 3, 4, 5 and 6 mol % to NaAMPS. FIG. 4 shows results measured in each gel. FIG. 5 shows variations in the number of spreading cells with time with respect to NaAMPS6 (♦ by dotted lines in FIG. 5).

COMPARATIVE EXAMPLE 1

A gel was prepared and the number of spreading cells among endothelial cells was measured in the same way as in example 1, except that AA(Mw=72.01, d=1.05 g/ml, Tokyo Kasei Kogyo Co.,Ltd.) was substituted for NaSS, and that crosslinking agent MBAA was mixed into AA in 2 mol % to AA. FIG. 5 shows variations in the number of spreading cells with time on the gel having a network structure comprised of a synthetic polymer that is a copolymer of AA and MBAA with the degree of crosslinking of 2 mol % (PAA2, ▲ in FIG. 5).

COMPARATIVE EXAMPLE 2

A gel was prepared and the number of spreading cells among endothelial cells was measured in the same way as in example 1, except that DMAAm was substituted for NaSS, and that crosslinking agent MBAA was mixed into DMAAm in 4 mol % to DMAAm. FIG. 5 shows variations in the number of spreading cells with time on the gel having a network structure comprised of a synthetic polymer that is a copolymer of DMAAm and MBAA with the degree of crosslinking of 4 mol % (DMAAm4, ▼ in FIG.5).

COMPARATIVE EXAMPLE 3

A gel was prepared and the number of spreading cells among endothelial cells was measured in the same way as in example 1, except that vinyl alcohol (Wako Pure Chemicals Industries Ltd.) was substituted for Nass, and that crosslinking agent MBAA was mixed into vinyl alcohol in 6 mol % to vinyl alcohol. FIG. 5 shows variations in the number of spreading cells with time on the gel having a network structure comprised of a synthetic polymer that is a copolymer of vinyl alcohol and MBAA with the degree of crosslinking of 6 mol % (PVA6, ♦ by alternate long and short dashed lines in FIG.5).

REFERENCE EXAMPLE

FIG. 5 shows variations in the number of spreading cells on the surface of a Petri dish with time when collagen gel was coated on the surface of the dish without being mottled.

In FIG. 5, by comparing the number of spreading cells on NaSS10 or NaAMPS6 with the number of spreading cells on PAA2, it is understood that any gels having a network structure comprised of the synthetic polymer that is a copolymer of NaSS or NaAMPS and MBAA according to the present invention have the spreading rate of endothelial cell twice as high and the number of endothelial cells adsorbed per unit twice as many as the gel having a network structure comprised of conventional synthetic polymer PAA2 that is a copolymer of AA and MBAA.

EXAMPLE 3

In example 3, gels obtained by copolymerizing NaAMPS and DMAAm were prepared such that molar fraction $F_{NaAMPS}$ of NaAMPS to total of NaAMPS and DMAAm is 0, 0.05, 0.1, 0.2, 0.3, 0.4, 0.5, 0.7 or 1.0. In addition, in this example, the degree of crosslinking of the gel, i.e. an amount of crosslinking agent MBAA to the total amount of NaAMPS and DMAAm, was adjusted to be 4 mol % in all the gels, the gels were thus prepared in the same way as in example 1 except other respects described particularly, and measurements were carried out on the number of spreading cells and so on with respect to endothelial cells using the prepared gels.

Figure 6B:
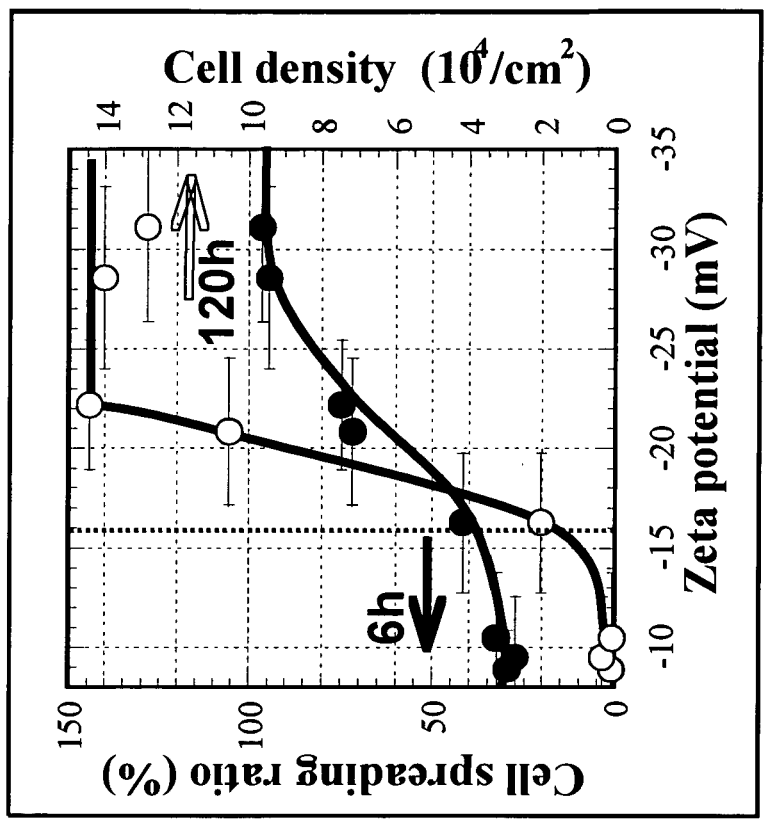
FIG. 6B is graphs showing spreading states of endothelial cells in 6-hour culture and 120-hour culture in each gel with different FNaAMPS in example 3.
Figure 6A:
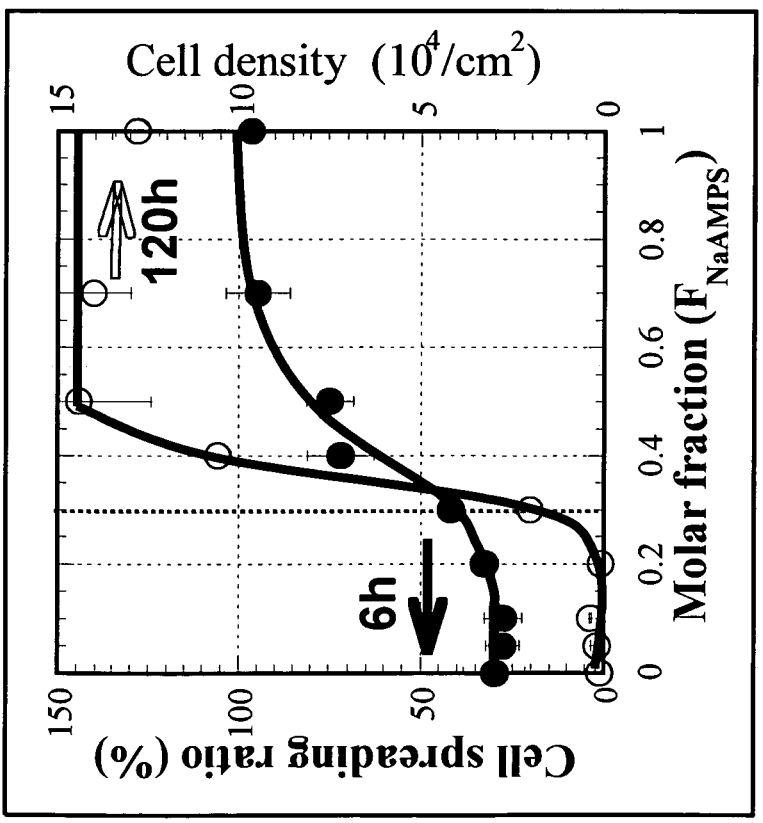
FIG. 6A is graphs showing spreading states of endothelial cells in 6-hour culture and 120-hour culture in each gel with different FNaAMPS in example 3.

FIG. 6A shows measurement results of the spreading ratio (of "the number of spreading cells" to "the number of set cells" (%): ● in FIG. 6A) at the time the endothelial cells were cultured for 6 hours, and the number of spreading cells (on a basis of $10^4$ cells/cm$^2$: ○ in FIG. 6A) at the time the cells were cultured for 120 hours, on the gels with respective different $F_{NaAMPS}$ prepared in this example. FIG. 6B shows results where $F_{NaAMPS}$ was converted into zeta potential and re-plotted on the gels with respective different $F_{NaAMPS}$.

It is understood from FIG. 6A that in a range of 0 to 0.3 of $F_{NaAMPS}$, the endothelial cells spread at the spreading ratio of 30 to 40% at the time of 6-hour culture, but the spread endothelial cells were almost killed at the time of 120-hour culture. Meanwhile, it is understood that in a range 0.3 to 1.0 of $F_{NaAMPS}$, the endothelial cells were not killed even at the time of 120-hour culture. Accordingly, based on the measurement results as shown in FIG. 6A, since it is estimated that a critical value of $F_{NaAMPS}$ on whether endothelial cells can be cultured to confluent or not exists around 0.3 (=$F_{NaAMPS}$), the molar fraction of NaAMPS is preferably 30 mol % or more in the gel in the case of culturing bovine fetal aorta endothelial cells using the gel obtained by copolymerizing NaAMPS and DMAAm. In addition, as can be seen from FIG. 6B, 0.3 of $F_{NaAMPS}$ corresponds to 16 mV of zeta potential.

EXAMPLE 4

In example 4, gels obtained by copolymerizing NaSS and DMAAm were prepared such that molar fraction $F_{NaSS}$ of NaSS to total of NaSS and DMAAm is 0, 0.05, 0.06, 0.075, 0.1, 0.2, 0.3, 0.4, 0.5, 0.6, 0.7, 0.8, 0.9 or 1.0. In addition, in this example, the degree of crosslinking of the gel, i.e. an amount of crosslinking agent MBAA to the total amount of NaSS and DMAAm, was adjusted to be 4 mol % in all the gels, the gels were thus prepared in the same way as in example 1 except other respects described particularly, and measurements were carried out on the number of spreading cells and so on with respect to endothelial cells using the prepared gels.

Figure 7:
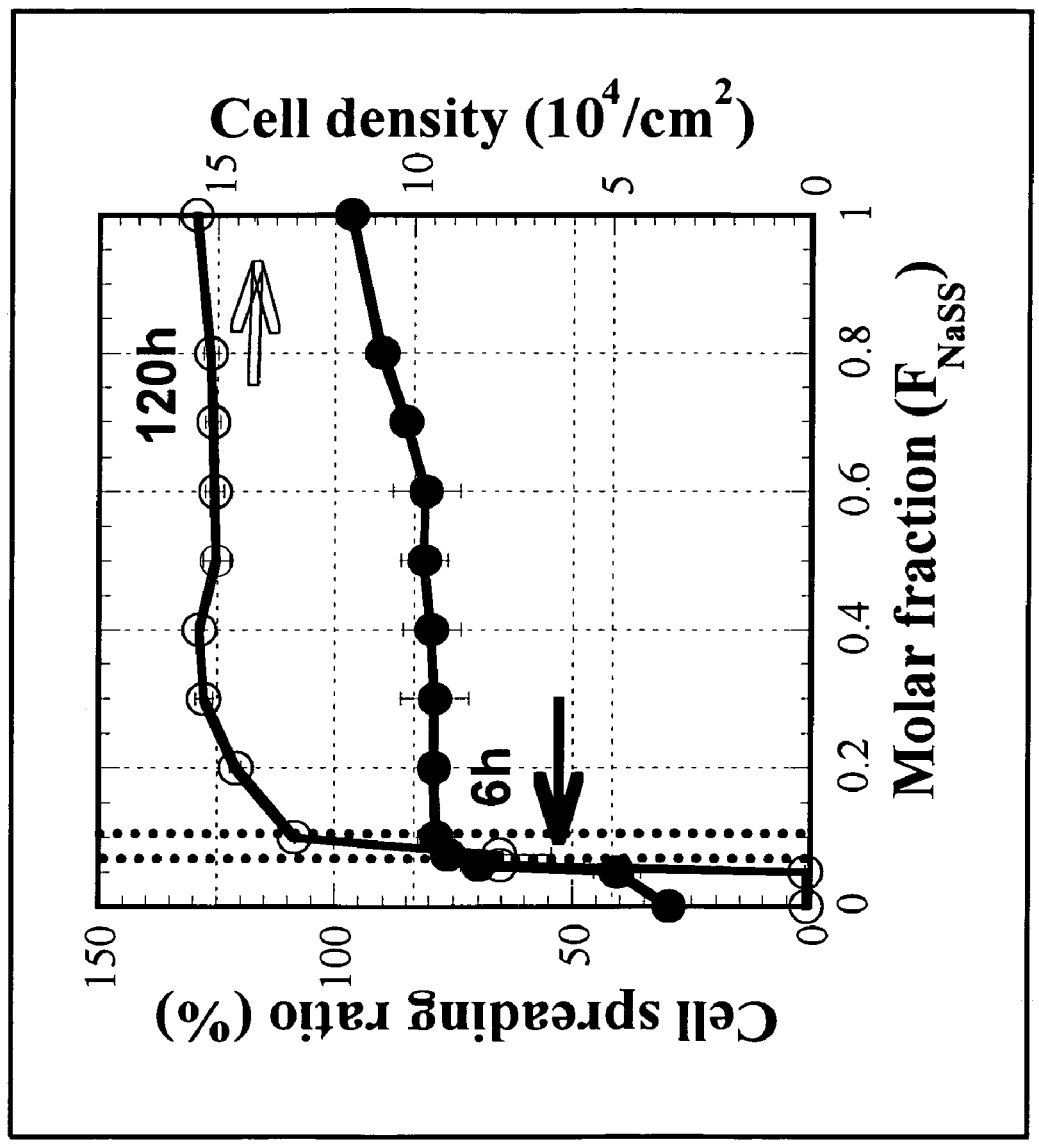
FIG. 7 is a graph showing spreading states of endothelial cells in 6-hour culture and 120-hour culture in each gel with different FNaSS in example 4.

FIG. 7 shows measurement results of the spreading ratio (of "the number of spreading cells" to "the number of set cells" (%): ●) at the time the endothelial cells were cultured for 6 hours, and the number of spreading cells (on a basis of $10^4$ cells/cm$^2$: ○) at the time the cells were cultured for 120 hours, on the gels with respective different $F_{NaSS}$ prepared in this example.

It is understood from FIG. 7 that in a range of 0.1 to 1.0 of FNaSS, the endothelial cells spread to almost confluent at the time of 120-hour culture. Meanwhile, it is understood that in $F_{NaAMPS}$=0, the endothelial cells did not spread even after being cultured for 120 hours. Accordingly, based on the measurement results as shown in FIG. 7, it is estimated that $F_{Nass}$ has a critical value, on whether endothelial cells can be cultured to confluent or not, in a range of 0 to 0.1. Therefore, in example 5 described below, it was examined what differences specifically occurred in culture of endothelial cell in a range of 0 to 0.1 of $F_{NaSS}$.

EXAMPLE 5

In example 5, using respective gels with molar fraction $F_{NaSS}$ of NaSS to total of NaSS and DMAAm of 0, 0.05, 0.06, 0.075, and 0.1 prepared in example 4, endothelial cells were cultured and the number of spreading cells was measured at 6, 24, 48, 72, 96 and 120 hours after initiation of culture.

Figure 8:
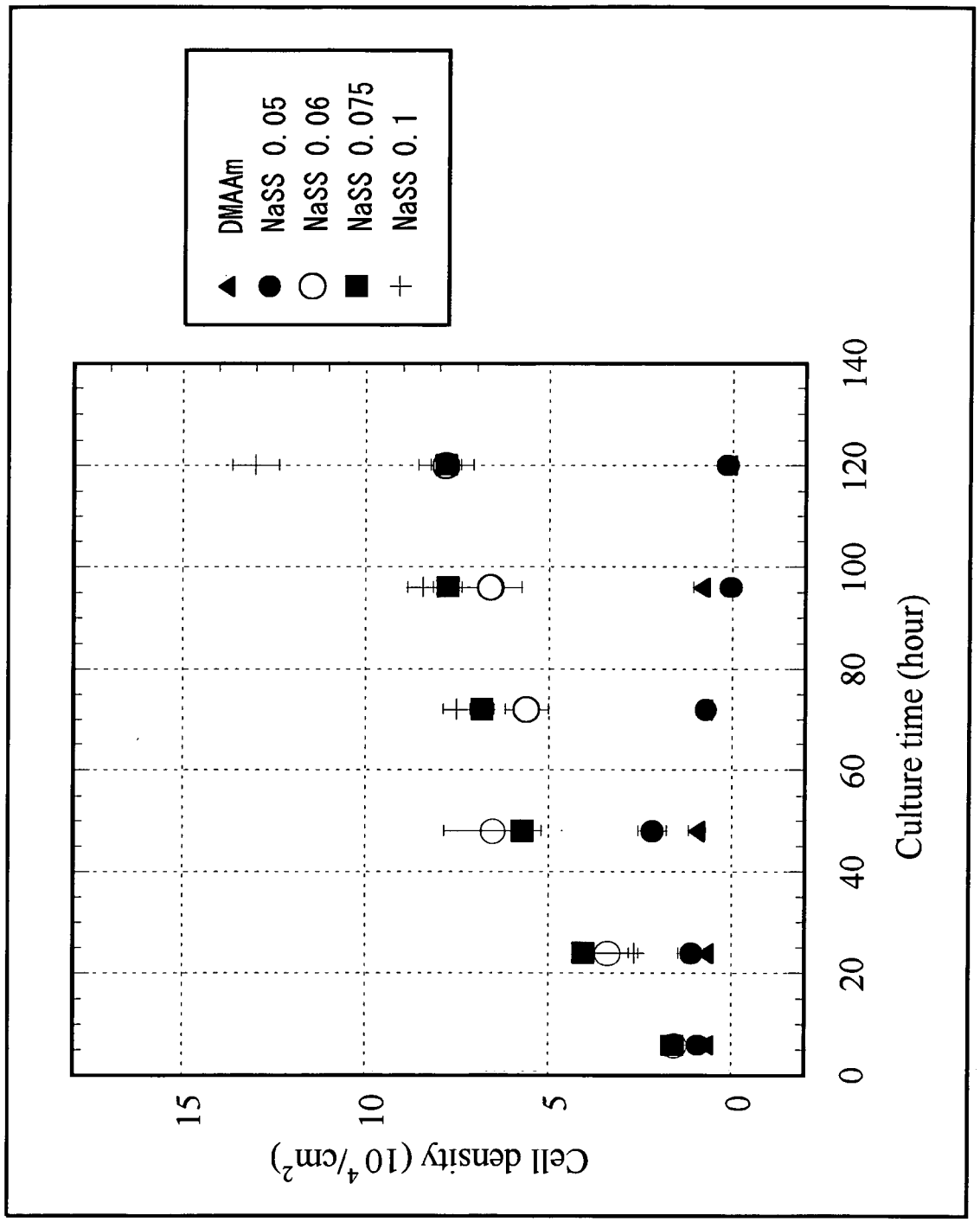
FIG. 8 is a graph showing spreading states of endothelial cells for each elapsed culture time in each gel with different FNaSS in example 5.

FIG. 8 shows measurement results of the number of spreading cells (X×$10^4$ cells/cm$^2$) of the gels with different values of $F_{NaSS}$ where the values of $F_{NaSS}$ are 0 (▲), 0.05 (●), 0.06(○), 0.075 (■), and 0.1 (+).

It is understood from FIG. 8 that in a range of 0 to 0.05 of $F_{NaSS}$, the endothelial cells did not spread, while not being killed, even when cultured for 120 hours. Meanwhile, it is understood that in a range of 0.06 to 0.075 of $F_{NaSS}$, the endothelial cells continued to proliferate to confluent certainly, while the spreading rate of endothelial cell was lower than in the case of $F_{NaSS}$=0.1. Accordingly, based on the measurement results as shown in FIG. 8, since it is estimated that a critical value of $F_{NaSS}$ on whether endothelial cells can be cultured to confluent or not exists around 0.06 (=$F_{NaSS}$), the molar fraction of NaSS is preferably 6 mol % or more in the gel in the case of culturing bovine fetal aorta endothelial cells using the gel obtained by copolymerizing NaSS and DMAAm.

EXAMPLE 6

In example 6, two types of gels were prepared with an interpenetrating polymer network structure or semi-interpenetrating polymer network structure, endothelial cells were cultured using the prepared gels, and at the time of 6-hour culture, surfaces of the gels were observed to measure the adsorption ratio (of "the number of adsorbed cells" to "the number of set cells" (%)) and spreading ratio (of "the number of spreading cells" to "the number of set cells" (%) ) of the endothelial cells. The two types of gels were prepared as described below. In this example, the gels were prepared in the same as in example 1, except respects described particularly, the endothelial cells were cultured, and measurements were carried out on the adsorption ratio and spreading ratio of the endothelial cells.

<Preparation of Gel 1>

As in example 2, the mixture solution of NaAMPS and crosslinking agent MBAA was prepared such that the degree of crosslinking was 4 mol %, and heated, whereby a first-stage gel was prepared which had a network structure comprised of NaAMPS and MBAA. The first-stage gel was immersed into 3 mol/L of DMAAm monomer solution to reach an equilibrium swollen state. The first-stage gel impregnated with DMAAm was heated to polymerize DMAAm by heat, and a second-stage gel was thereby prepared. Further, the second-stage gel was immersed into the mixture solution used in preparing the first-stage gel to reach an equilibrium swollen state. The second-stage gel impregnated with the mixture solution was heated to polymerize NaAMPS and crosslinking agent MBAA by heat, and a third-stage gel, i.e. gel 1 was thereby prepared.

<Preparation of Gel 2>

The second-stage gel in preparation of gel 1 in this example was immersed into 1 mol/L of NaAMPS monomer solution without crosslinking agent MBAA to reach an equilibrium swollen state. The second-stage gel impregnated with the monomer solution of NaAMPS was heated to polymerize NaAMPS by heat, and a third-stage gel, i.e. gel 2 was thereby prepared. Accordingly, the difference between gel 1 and gel 2 in this example is that in gel 1, the network structure of NaAMPS (indicated by "PNaAMPS" in the lowerportion in FIG. 9) forming the uppermost layer of the surface of the gel was crosslinked with MBAA with the degree of crosslinking of 4 mol %, while in gel 2, NaAMPS forming the uppermost layer of the surface of the gel was not crosslinked with MBAA.

Figure 9:
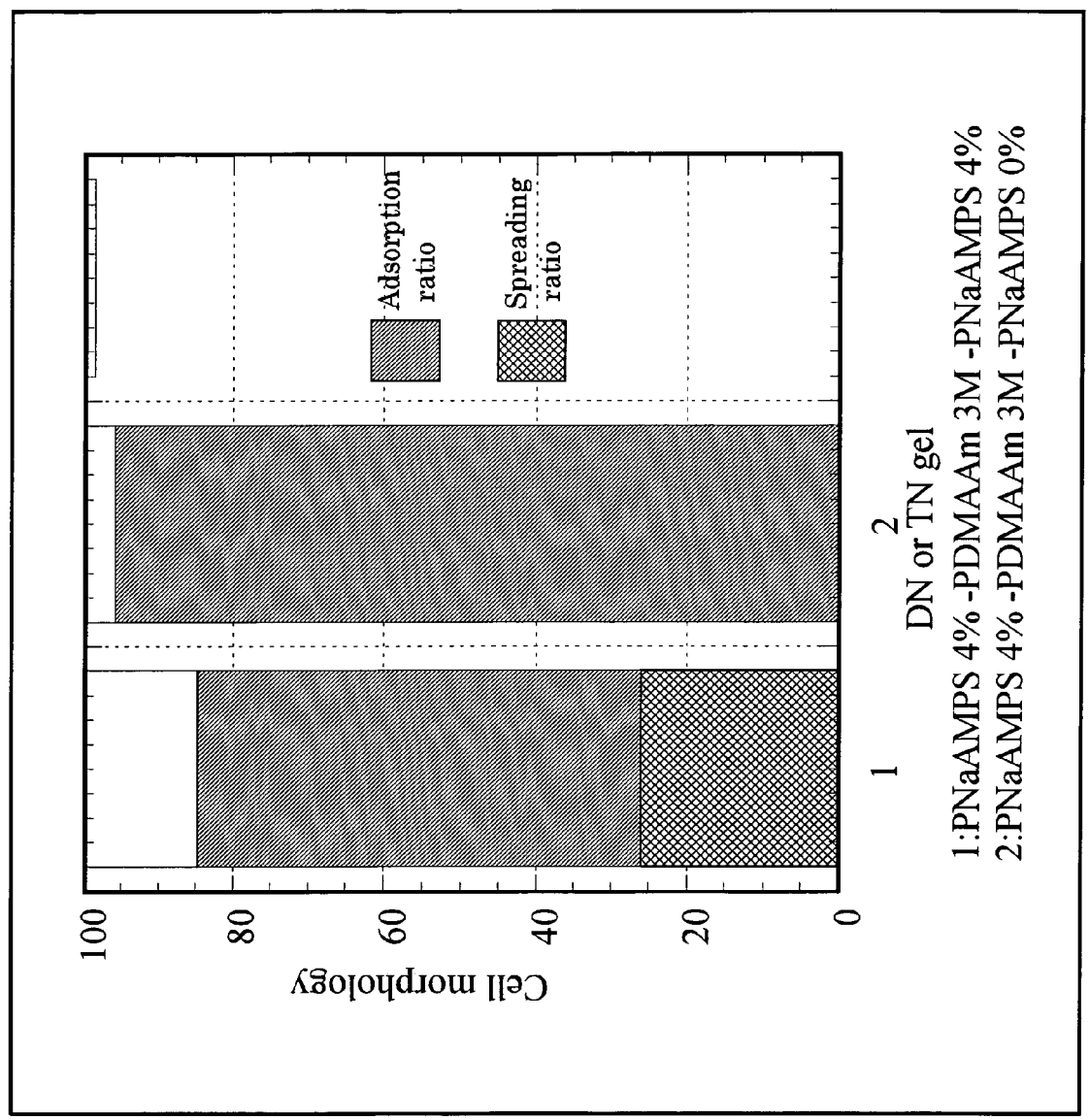
FIG. 9 is a graph showing an adsorption rate and spreading rate of endothelial cells in 6-hour culture in each of gel 1 and gel 2 in example 6.

FIG. 9 shows measurement results of gel 1 and gel 2 on the number of adsorption ratio and spreading ratio of endothelial cells at the time the endothelial cells were cultured for 6 hours after being set on the surface of gel 1 or gel 2 prepared in this example, respectively.

As can be seen from FIG. 9, the endothelial cells spread up to the spreading ratio of 26% in gel 1, while the endothelial cells did not spread at all in gel 2. It is understood from these results that characteristics of the network structure constituting the uppermost layer of the surface of the gel are important for endothelial cells to spread, and that the network structure needs the degree of crosslinking to some extent.

As described above, according to the present invention, a cell culture scaffold contains a gel having a network structure comprised of a synthetic polymer obtained by polymerization or copolymerization of a monomer having a sulfonic group, and it is thereby possible to provide cell culture scaffold with low manufacturing cost and high yield (the number of cultured cells) per unit area.

Further, according to the present invention, for example, by polymerizing or copolymerizing p-styrenesulfonic acid alkali metal salt or 2-acrylamide-2-methylpropane sulfonic acid alkali metal salt, the network structure comprised of a synthetic polymer is formed, and it is thus possible to expand an allowable range of the degree of crosslinking in the synthetic polymer.

Furthermore, according to the present invention, since cells are cultured using the gel, it is possible to obtain in a short time a large number of cultured cells with uniform quality and no risk of virus infection.

The cell culture scaffold according to the present invention is useful as scaffold for cells such as chondrocyte, fibrocyte, smooth muscle cell, endothelial cell, and epithelial cell. Further, in the cell culture scaffold according to the present invention, the surface of the gel can be used in three dimensions by being processed to particles or porous member, it is thereby possible to culture cells in high density, and therefore, the scaffold are valuable in culture of cells that produce a useful substance such as a protein and polysaccharide particularly when cultured in high density. Furthermore, the cell culture scaffold according to the present invention can be used as artificial organs such as an artificial vessel with cultured cells adhered to the surface, and therefore, are useful as a complex material for medical equipment.

The present invention is not limited to the above described embodiments, and various variations and modifications may be possible without departing from the scope of the present invention.

This application is based on the Japanese Patent Application No. 2004-194412 filed on Jun. 30, 2004, and the Japanese Patent Application No. 2005-2976 filed on Jan. 7, 2005, entire content of which is expressly incorporated by reference herein.

What is claimed is:

1. A scaffold for culturing cells containing a gel comprising a synthetic polymer obtained by copolymerization of p-styrenesulfonic acid alkali metal salt and dimethyl acrylamide, wherein the molar fraction of p-styrenesulfonic acid alkali metal salt to the total of p-styrenesulfonic acid alkali metal salt and dimethyl acrylamide is 6 mol % or more.

2. A scaffold for culturing cells containing a gel comprising a synthetic polymer obtained by copolymerization of p-styrenesulfonic acid alkali metal salt and dimethyl acrylamide, wherein the molar fraction of p-styrenesulfonic acid alkali metal salt to the total of p-styrenesulfonic acid alkali metal salt and dimethyl acrylamide is about 6 to 90 mol %.

3. A scaffold for culturing cells containing a gel comprising a synthetic polymer obtained by copolymerization of 2-acrylamide-2-methylpropane sulfonic acid alkali metal salt and dimethyl acrylamide, wherein the molar fraction of 2-acrylamide-2-methylpropane sulfonic acid alkali metal salt to the total of 2-acrylamide-2-methyipropane sulfonic acid alkali metal salt and dimethyl acrylamide is 30 mol % or more.

4. A scaffold for culturing cells containing a gel comprising a synthetic polymer obtained by copolymerization of 2-acrylamide-2-methylpropane sulfonic acid alkali metal salt and dimethyl acrylamide, wherein the molar fraction of 2-acrylamide-2-methyipropane sulfonic acid alkali metal salt to the total of 2-acrylamide-2-methylpropane sulfonic acid alkali metal salt and dimethyl acrylamide is about 30 to 70 mol %.

5. A scaffold for culturing cells containing a gel comprising a synthetic polymer obtained by copolymerization of p-styrenesulfonic acid alkali metal salt, dimethyl acrylamide and crosslinking reagent, wherein:

the molar fraction of p-styrenesulfonic acid alkali metal salt to the total of p-styrenesulfonic acid alkali metal salt and dimethyl acrylamide is 6 mol % or more, and the amount of crosslinking reagent to the total of p-styrenesulfonic acid alkali metal salt and dimethyl acrylamide is in a range of 0.1 to 10 mol %.

6. A scaffold for culturing cells containing a gel comprising a synthetic polymer obtained by copolymerization of 2-acrylamide-2-methylpropane sulfonic acid alkali metal salt, dimethyl acrylamide and crosslinking reagent, wherein:

the molar fraction of 2-acrylamide-2-methylpropane sulfonic acid alkali metal salt to the total of 2-acrylamide-2-methylpropane sulfonic acid alkali metal salt and dimethyl acrylamide is 30 mol % or more, and the amount of crosslinking reagent to the total of 2-acrylamide-2-methylpropane sulfonic acid alkali metal salt and dimethyl acrylamide is in a range of 0.1 to 10 mol %.

7. A method for culturing cells including the step of culturing cells on the scaffold according to claim 1.

8. A method for culturing cells including the step of culturing cells on the scaffold according to claim 4.

* * * * *